United States Patent [19]
DiMarchi et al.

[11] Patent Number: 5,622,932
[45] Date of Patent: Apr. 22, 1997

[54] IGF-1 SUPERAGONISTS

[75] Inventors: Richard D. DiMarchi, Carmel, Ind.; Li Fan, Lombard, Ill.; Harlan B. Long, Carmel, Ind.

[73] Assignee: Eli Lilly and Company, Indianapolis, Ind.

[21] Appl. No.: 435,252

[22] Filed: May 5, 1995

[51] Int. Cl.$^6$ .................................................. C07K 14/65
[52] U.S. Cl. .............................. 514/12; 514/21; 530/324; 530/399
[58] Field of Search .................. 514/12, 21; 530/399, 530/324

[56] References Cited

FOREIGN PATENT DOCUMENTS

| | | |
|---|---|---|
| 0436469 | 12/1990 | European Pat. Off. . |
| WO91/12018 | 8/1991 | WIPO . |
| WO92/02245 | 2/1992 | WIPO . |
| WO95/16708 | 6/1995 | WIPO . |

OTHER PUBLICATIONS

Humbel, European Journal of Biochemistry, 190, pp. 445–462 (1990).
DiMarchi et al, Peptides=Chemistry and Biology; Proceedings of the 12th American Peptide Symposium, Jun. 16–21, 1991 (1992) pp. 26–28, Smith and Rivier, eds.
Cascieri et al, Biochemistry 27:3229–3233 (1988).
Bayne et al, J. Biol. Chem. 249:11004–11008 (1988).
Zoler, M.L., *Medical World News*, 12 (1991).

*Primary Examiner*—Howard E. Schain
*Attorney, Agent, or Firm*—Ronald S. Maciak; David E. Boone

[57] ABSTRACT

The instant invention provides two-chain IGF-1 superagonists which are derivatives of the naturally occurring single-chain IGF-1 having an abbreviated C domain. The invention also provides synthetic and semi-synthetic DNA sequences, recombinant DNA vectors and transformed host cells useful in the recombinant production of these analogs. The invention also provides pharmaceutical formulations comprising these IGF-1 analogs. The invention also provides methods of using these analogs in a variety of therapeutic applications. The instant invention provides IGF-1 analogs of the formula:

$$BC^nA \qquad (1)$$

wherein:
- B is the B domain of IGF-1 or a functional analog thereof,
- C is the C domain of IGF-1 or a functional analog thereof,
- n is the number of amino acids in the C domain and is from about 6 to about 12, and
- A is the A domain of IGF-1 or a functional analog thereof.

9 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr
            20                  25

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

Gly Tyr Gly Ser Ser Ser Arg Arg Ala Pro Gln Thr
1               5                   10

( 2 ) INFORMATION FOR SEQ ID NO:3:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

Gly Ile Val Asp Glu Cys Cys Phe Arg Ser Cys Asp Leu Arg Arg Leu
1               5                   10                  15

Glu Met Tyr Cys Ala
            20

IGF-1 SUPERAGONISTS

FIELD OF THE INVENTION

The present invention relates to synthetic peptides possessing insulin and IGF-1 activity. The invention also relates to recombinant DNA compounds, vectors and transformed cell lines useful in the production of said peptides. The invention also relates to methods of using said compounds in the treatment of human afflictions. The invention also relates to pharmaceutical formulations comprising said compounds.

BACKGROUND OF THE INVENTION

IGF-1, also known as somatomedin C, is a serum polypeptide which mediates the activity of growth hormones and also possesses insulin-like activity. Humbel, R. E. (990) European Journal of Biochemistry. 190, 445–462 "Insulin-like Growth Factors I and II" IGF-1 has known insulin-like potency and stimulation potency of sulphate uptake by cartilage, and it may enhance protein and DNA synthesis in cells. It is therefore useful as a growth promoter and for the treatment of diabetes. IGF-1 may be used in humans to treat growth hormone deficiencies, in farm animals to increase growth rates, increase the relative proportion of muscle or improve food conversion efficiency in humans to suppress the loss of body protein in severe catabolic states such as following burns, infection or other trauma, in humans and animals to improve wound healing and to support the growth of cells in culture. IGF-1 may be used for the treatment of disorders associated with tissue wasting including burns, skeletal trauma, infection, cancer, cystic fibrosis, Duchenne muscular dystrophy, Becker dystrophy, autosomal recessive dystrophy, polymyositis as well as other myopathies and AIDS. IGF-1 may be used for the treatment of protein accumulation deficiencies in mammals. Specific deficiencies are those associated with infant prematurity, growth hormone deficiency, somatomedin deficiency, burns, infection, other trauma, cancer, cystic fibrosis, Duchenne muscular dystrophy, Becker dystrophy, autosomal recessive dystrophy, polymyositis, as well as other myopathies and AIDS. IGF-1 may be used to stimulate erythropoiesis and is therefore useful in humans for treating growth deficiencies and for restricting negative nitrogen balance associated with catabolic conditions. Consequently, it is desirable to have IGF-1 analogs possessing greater than natural activity.

These analogs are of applicable importance for treatment of catabolic states such as diabetes where there is a deficiency in both insulin and IGF-1 activity.

The structure-activity relationship of IGF-1 has been approached from synthetic, semisynthetic, and biosynthetic methods. DiMarchi, et al. reported the importance of C domain to the attainment of full IGF-1 receptor affinity. "Synthesis of a fast acting insulin based on structural homology with insulin-like growth factor I", DiMarchi, R. D., et al. in *Peptides: Chemistry and Biology; Proceedings of the Twelfth American Peptide Symposium, Jun. 16–21, 1991 Cambridge* Mass., (1992) Smith, J. A. and Rivier, J. E. eds., pp.26–28 ESCOM, Leiden. The two-chain IGF-1 equivalent of insulin was reported to possess nearly equal affinity for the insulin and IGF-1 receptor. Additional two-chain IGF-1 related peptides that possess appreciable substitutions with insulin residues have been prepared. In all instances the potency of these heterodimeric IGF-1 species have displayed reduced affinity for the IGF-1 receptor relative to that of the analogous IGF-1 ligand. Biosynthesis of IGF-1 analogs has been exclusively focused on single-chain peptides. Cascieri, M. A., et i. (1988) Biochemistry 27:3229–3233; Bayne, M. L. et al. (1988) J. Biol. Chem. 249:11004–11008.

We have surprisingly observed that where complete removal of the C domain reduces IGF-1 potency, partial removal of the C domain in split IGF-1 molecules yields superagonists. This observation is in contrast to the insulin receptor where we observe a steady increase in insulin receptor affinity with sequential degradation of he C domain. The divergent performance at these two highly homogolous receptors was totally unexpected. It has provided unique IGF-1 analogs that are superagonists at the IGF-1 receptor and as an additional benefit possess significantly greater insulin potency than the natural

SUMMARY OF THE INVENTION

The instant invention provides two-chain IGF-1 superagonists which are derivatives of the naturally occurring single-chain IGF-1 having an abbreviated C domain. The invention also provides synthetic and semi-synthetic DNA sequences, recombinant DNA vectors and transformed host cells useful in the recombinant production of these analogs. The invention also provides pharmaceutical formulations comprising these IGF-1 analogs. The invention also provides methods of using these analogs in a variety of therapeutic applications.

DETAILED DESCRIPTION OF THE INVENTION

The instant invention provides IGF-1 analogs of the formula:

$$BC^n,A \quad (1)$$

wherein:

B is the B domain of IGF-1 or a functional analog thereof,

C is the C domain of IGF-1 or a functional analog thereof, n is the number of amino acids in the C domain and ranges from about 6 to about 12, and A is the A domain of IGF-1 or a functional analog thereof.

NOMENCLATURE:

Subunits of the IGF-1 molecule are denoted B, C, A, and D in upper case. Upper case B denotes the B domain of IGF-1. Upper case C denotes the C domain of IGF-1. Upper case A denotes the A domain of IGF-1. Upper case D denotes the D domain of IGF-1. The representation BCAD IGF-1 indicates that the primary amino acid sequence (from the amino to the carboxy terminus) is the sequence of the B domain of IGF-1 connected to the C domain of IGF-1 connected to the A domain of IGF-1 connected to the D domain of IGF-1 in a single contiguous peptide unit. The numbered amino acid residues, such as B(8) indicates the amino acid which occurs at position eight of the B domain of IGF-1. The numbering of particular residues in IGF-1 is in accordance with the conventionally ascribed numbering for this well known molecule. For instance in the above examples, even if the amino acid is not the eighth residue in the B domain of the particular analog under consideration, the designation B(8) will be retained for consistency. A comma in the structure (i.e., BC,A) indicates the presence of a break in the polypeptide backbone structure even though the molecule is held together by disulfide bonds. The absence of a letter from the full IGF-1 structure indicates that particular subunit is not present in the particular molecule under consideration. A superscript in the designation (i.e. $BC^{12}$,A) indicates the number of amino acids in that subunit, for instance a C domain with 12 amino acids. Lower case b and a denote the respective chains of insulin (b,a) and c denotes the connecting peptide that joins b and a in proinsulin (bca).

A number of IGF-1 and insulin constructions were made and assayed for IGF-1 activity. The activity of native human insulin and proinsulin are also included for purposes of comparison. The results are summarized in Table I below.

TABLE I

Activity of IGF-1 Analogs

| CONSTRUCT[1] | % IGF-1 POTENCY[2] | % INSULIN POTENCY[2] | RATIO[3] |
| --- | --- | --- | --- |
| BCAD (IGF-1) | 100 | 1.2 | 83 |
| BCA | 77 | 2.4 | 32 |
| $BC^{12}$*,A | 127 | 9.8 | 13 |
| $BC^{10}$*,A | 186 | 16 | 12 |
| $BC^{8}$*,A | 141 | 16 | 8.8 |
| $BC^{6}$*,A | 57 | 18 | 3.2 |
| B,A | 7.7 | 18 | 0.43 |
| b,a (insulin) | 0.37 | 100 | 0.0037 |
| bca (proinsulin) | <0.1 | 2.4 | <0.41 |

[1]All constructs use the naturally occurring human peptide sequences.
[2]Measured in accordance with the teaching of Example 5.
[3]RATIO = IGF-1 POTENCY ÷ INSULIN POTENCY
*In these examples, the superscript refers to the residues in the C-domain beginning with the N-terminal residue through the residue number corresponding to the superscript.

The above data clearly show that an "opened" (i.e. 2-chain) derivative of IGF-1 which retains the C domain is much more active than the single-chain IGF-1 molecule. The data also indicate that the presence of a C domain of more than 6 amino acids is essential for full potency at the IGF-1 receptor. Approximately 10±2 residues appears to be the optimum length for the C domain relative to native BCAD (IGF-1). It is important to note that the C domain is essential for IGF-1 activity but not for insulin activity. Indeed, insulin potency is maximized with shortening of the IGF-1 C domain by 6 amino acids and does not change upon further deletion.

A comparison of the naturally occurring peptides b,a (insulin) and BCAD (IGF-1) with one another in the context of the analogs demonstrates that there is a clear molecular basis for the structural differences. The absence of the IGF-1 C domain in the construct B,A when compared to a single-chain IGF-1 (BCA) demonstrates that the C domain is essential for interaction with the IGF-1 receptor. As the size of the C domain diminishes (below 10), the ability of the two-chain IGF-1 analog's binding affinity to IGF-1 receptor concomitantly decreases. Of additional importance is the recognition that the insulin receptor affinity can simultaneously change with that for the IGF-1 receptor. Consequently, it can be concluded that the C domain of IGF-1 serves an important function in providing high affinity recognition and selectivity to the IGF-1 receptor. Insulin receptor affinity is regulated predominantly by covalent attachment of C domain to A domain, and to a lesser extent by the linear size of the C domain. The importance of this latter feature is exemplified where the closure of the $BC^{12}$,A to the naturally occurring single-chain version yields a slight reduction in IGF-1 receptor affinity with a significant increase in receptor selectivity. C domains extending beyond 10-residues have reduced potencies. Examples include $BC^{12}$,A relative to $BC^{10}$,A and bca relative to b,a.

The insulin and IGF-1 receptors appear to share certain biological functions. Each receptor is capable of mediating metabolic and mitogenic cellular activities. Acute catabolic physiological conditions, such as that resulting from surgical interventions, can be reversed through the administration of IGFs and insulin. Similarly, optimal therapy for chronic catabolic states, such as diabetes require normalization of such hormonal factors as insulin and IGF-1.

We have surprisingly observed that peptides with greater potency than IGF-1 itself can be derived through the preparation of heterodimeric IGF-1 constructs. The single split in the BCA chain between the junction of the C and A domains yields a unique and novel IGF-1 peptide of nearly twice the potency of the single-chain comparator BCA.

The 2-chain IGF-1 analogs have an additional virtue when compared to single-chain peptides. These peptides have appreciably greater insulin potency. The near-optimal size for maximal insulin potency is quickly realized with a shortening of the C domain by 2–6 residues. The IGF-1 potency increases with initial C domain deletion to a point of maximal potency when C domain is 10 amino acids in length. Further shortening of the sequence decreases the IGF-1 potency. The single novel and unique IGF-peptide $BC^{10}$,A appears to present a best combination for maximal IGF-1 and insulin potency. IGF-1 analogs of this type present the unique virtues when compared to IGF-1 of being more potent at the IGF-1 receptor and capable of simultaneously bestowing greater insulin action.

The invention further provides functional analogs of the IGF-1 analogs of Formula 1. Functional analog refers to a molecule having similar functional properties but a modified structure relative to the naturally occurring form of that molecule or compound. Functional analogs include fragments of (or additions to) the parent molecule having functional properties and reactivities similar to the parent molecule. Such functional analogs typically exhibit the same qualitative biological activity as the naturally-occurring peptide, although functional analogs may also be designed which significantly modify the characteristics of a peptide. Functional analogs are ordinarily engineered variations, but such functional analogs include naturally occurring allelic or interspecies variations of the peptide amino acid sequence.

Such functional analogs may be prepared by modification of the DNA encoding the IGF-1 analog and thereafter expressing the DNA in recombinant cell culture. Techniques for making substitutional mutations at predetermined sites in DNA having a known sequence are well known, for example M13 primer mutagenesis. The mutations that might be made in the DNA encoding the functional analog peptide must not place the sequence out of the reading frame and preferably will not create complementary regions that could produce secondary mRNA structure.

Functional analogs of IGF-1 are generally created by modification of the amino acid sequence of the peptide in a specific and limited manner. While the site for introducing an amino acid sequence variation is predetermined, the mutation se need not be predetermined. For example, in order to optimize the performance of a mutation at a given site, random mutagenesis may be conducted at the target codon or region and the resulting functional analogs screened for the optimal combination of desired activity.

Functional analogs of the peptides are typically generated by deletion, insertion, or substitutions of a single (or few) amino acid residue (s). Such modifications with naturally occurring amino acids generally are made in accordance with the following Table II:

TABLE II

| Original Residue | Exemplary Substitutions |
|---|---|
| Ala | Ser |
| Arg | Lys |
| Asn | Gln; His |
| Asp | Glu |
| Cys | Ser; Ala |
| Gln | Asn |
| Glu | Asp |
| Gly | Pro; Ala |
| His | Asn, Gln, Lys |
| Ile | Leu; Val |
| Leu | Ile; Val |
| Lys | Arg; Glu |
| Met | Leu; |
| Phe | Leu; Tyr |
| Ser | Thr, Asn |
| Thr | Ser, Asn, Val |
| Trp | Tyr |
| Tyr | Trp; Phe |
| Val | Ile; Leu |

Substantial changes in function or immunological identity can arise by selecting substitutions that are less conservative than those in Table II, i.e., selecting residues that differ more significantly in their effect on maintaining (a) secondary or tertiary structure of the polypeptide backbone, (b) the charge or hydrophobicity of the residue, or (c) the bulk of the side chain. The substitutions which in general are expected to produce the greatest changes in peptide properties will be those in which (a) a hydrophilic residue is substituted by a hydrophobic residue; (b) a cysteine or proline is substituted for any other residue; (c) a residue having a charged side chain is substituted for a neutral residue; or (d) a residue having a hydrophobic side chain is substituted for one of small hydrophobic side chain changing the stereochemistry at the alpha-carbonyl.

A variety of amino acid modifications have been introduced into the primary structure of IGF-1. These functional analogs have demonstrated a wide variety of desirable characteristics useful for treating various forms of diabetes, to facilitate commercial (especially recombinant) production, and/or to provide more desirable pharmaceutical formulations. Applebaum, et al. (U.S. Pat. No. 4,876,242 issued Oct. 24, 1989) describes human IGF-1 analogs which possess higher levels of IGF-1 activity due to reduced affinity for serum components while retaining affinity to type I receptor. Ueda, et al. U.S. Pat. No 4,745,179 issued May 17, 1988) describes a $Val_{59}$-IGF-1 analog that simplifies production through application of cyanogen bromide. Bayne and Cascieri (European Patent Application No. EP-379338-A published Jul. 25, 1990) describe an analog of human IGF-1 reportedly retaining efficient binding to the type-I insulin receptor but shows reduced binding to 28K IGF binding proteins. The IGF analog described therein is reportedly 100 times more potent than natural IGF-1 in stimulating DNA synthesis in 3T3 cells. A number of other patents, patent applications and publications are readily available to the skilled artisan to determine modifications to the primary structure of the compounds of Formula 1 which would be useful. For example: Japanese patent application No. J01050899-A, published Feb. 27, 1989. (Sumitomo Seiyaku KK); U.S. Pat. No. 4,769,361 issued Sep. 6, 1988, Japanese patent application No. J01063597-A (Sumitomo Seiyaku KK); Japanese patent application No. J62190199-A (Fujisawa Pharmaceuticals KK); Japanese patent application No. J62169733-A (Fujisawa Pharmaceuticals KK); U.S. Pat. No. 5,070,075 (issued Dec. 3, 1991); U.S. Pat. No. 5,077, 276 (issued Dec. 31, 1991); and European Patent application No. EP-346429-A (published Dec. 20, 1989). The instant invention includes IGF-1 functional analogs of Formula 1 incorporating such known modifications to the structure of IGF-1 hybrid functional analogs.

In the preferred practice of the invention, the amino acid sequence of the subunits of the IGF-1 analog of Formula 1 is the naturally occurring amino acid sequence of the IGF-1 A domain, the naturally occurring sequence of the IGF-1 B domain, and a shortened version of the naturally occurring sequence of the IGF-1 C domain. Further embodiments of this invention may be directed to functional analogs of the IGF-1 molecule derived from alternate species such as monkey, porcine, bovine, guinea pig, fish or duck IGF-1 analogs. In a further preferred embodiment of the invention as exemplified herein, B, C, and A are derived from the natural sequence human IGF-1. In the most preferred practice of the invention as exemplified herein, the IGF-1 analog of Formula 1 comprises the structure $BC^{10},A$.

The IGF-1 analogs of Formula 1 may be constructed either:

a) through a single-chain IGF-1 precursor which is subsequently chemically and or enzymatically processed to yield the IGF-1 analog of interest, or b) through assembly of independent IGF-1 peptide subunit chains. A single-chain (BCA or BCAD) IGF-1 precursor and/or the independent B, C, A or D domains may be produced by solid phase peptide synthesis, solution phase peptide synthesis, or by recombinant DNA methods.

The intact IGF-1 molecule may be isolated from natural sources (See e.g. European Patent Application No. EP-209331-A, published Jan. 21, 1987, which describes the purification of IGF-1 from natural sources.).

Japanese patent application No. J01063597-A (Mar. 9, 1989) describes the synthesis of a IGF-1 derivatives by condensation of amino acid units.

The intact IGF-1 molecule may then be cleaved, either enzymatically or chemically, to obtain compounds of Formula 1.

The compounds of Formula 1 may also be made by independent solid phase or recombinant DNA production of the $BC^n$ and A domains independently and assembling the compounds of Formula 1 from the two subunits by techniques well known in the art in a manner analogous to the assembly of recombinant human insulin from two independent chains.

The techniques for solid phase peptide synthesis are well known in the art. See e.g., Gesellschen, P. D. and Santerre, R. F. "Synthesis of Peptides and Proteins by Chemical and Biotechnological Means", *Peptide and Protein. Drug Delivery*, Lee, V. H. L., ed. Chapter 2 (1991) Marcel Dekker, New York, N.Y. 10016; and generally *Methods in Enzymology*, v.185 (1990) Goeddel, D. V. ed.

IGF-1 analog peptides were synthesized by solid-phase methodology utilizing an Applied Biosystems 430A peptide synthesizer (commercially available from Applied Biosystems, Foster City, Calif. 94404). Boc amino acid resins and other reagents were supplied by Applied Biosystems and other commercial sources. Sequential Boc chemistry using double couple protocols and acetic anhydride capping were applied to the desired Boc-amino acid-4-(oxymethyl)phenylacetamidomethyl [PAM] resin. Asparagine, histidine, glutamine, arginine, [α-(p-hydroxyphenyl) acetic acids], [β-(p-hydroxyphenyl) propionic acids], p-hydroxybenzoic acids, p-hydroxycinnamic acids and p-hydroxyphenoxy acetic acids were coupled using preformed hydroxy benzotriazole esters. All other residues were coupled using preformed symmetrical anhydrides with dicyclocarbodiimde (DCC).

The following side chain protection was used:

Arg, tosyl
Asp, cyclohexyl
Cys, 4-methylbenzyl
Glu, cyclohexyl
His, benzyloxymethyl (BOM)
Lys, 2-chlorobenzyloxycarbonyl
Ser, benzyl
Thr, benzyl
Tyr, 2-bromobenzyloxycarbonyl Boc deprotection was accomplished with trifluoroacetic acid (TFA) in methylene chloride. Following completion of the synthesis the peptides were deprotected and cleaved from the resin with anhydrous hydrogen fluoride (HF) containing approximately 10% meta-cresol or 5% meta-cresol and 5% para-thiocresol. For peptidyl resins containing Met(O) a procedure using TFA, DMS, and HCl was followed prior to cleavage from the resin as described in Example 1. After removal of the HF, the peptide/resin was washed with ethyl ether, and the peptide sulfitolyzed as described in Examples 1 and 2. Disulfide pairing was conducted as described in Example 3. Purification was accomplished as indicated in Example 4.

Although synthesis of the peptides of Formula 1 may proceed by solid phase peptide synthesis or by recombinant methods, recombinant methods are preferred if a high yield is desired. The recombinant synthesis of IGF-1 has been reported. DiMarchi, et al. (1989) J. Cellular Biochemistry 86:283–294. The basic steps in the recombinant production of IGF-1 peptides include:

a) constructing a synthetic or semi-synthetic DNA encoding the IGF-1 analog of the Formula 1, b) integrating said DNA into an expression vector in a manner suitable for the expression of the IGF-1 analogs directly or as a fusion protein, c) transforming an appropriate eukaryotic or prokaryotic host cell with said expression vector, d) culturing said transformed or transfected host cell under conditions favorable to the production of the IGF-1 peptide, and e) recovering and purifying the recombinantly produced IGF-1 analog If one elects to produce the IGF-1 molecule (or independent subunits) by recombinant means, it is necessary to obtain a DNA sequence encoding the IGF-1 precursor of interest. The DNA coding sequence may be wholly synthetic, semi-synthetic or the result of modification of the native IGF-1 cDNA. Synthetic genes, the in vitro or in vivo transcription and translation of which will result in the production of IGF-1 peptides may be constructed by techniques well known in the art. Owing to the natural degeneracy of the genetic code, the skilled artisan will recognize that a sizable, yet definite number of DNA sequences may be constructed which encode IGF-1 peptides. The gene encoding the IGF-1 peptides may be created by synthetic methodology. Such methodology of synthetic gene construction is well known in the art. Brown, et al. (1979) Methods in Enzymology, Academic Press, N.Y., Vol. 68, pgs. 109–151. The DNA sequence corresponding to the synthetic IGF-1peptides gene may be generated using conventional DNA synthesizing apparatus such as the Applied Biosystems Model 380A or 380B DNA synthesizers (commercially available from Applied Biosystems, Foster City, Calif.).

Ueda, et al, (U.S. Pat. No. 5,019,500 issued May 8 1991) describes synthetic genes useful for recombinant production of human IGF-1.

Construction of suitable vectors containing the desired coding and control sequences employ standard ligation techniques. Isolated plasmids or DNA fragments are cleaved, tailored, and religated in the form desired to form the plasmids required. To effect the translation of the desired IGF-1 peptide, one inserts the IGF-1 peptide DNA coding sequence in an appropriate recombinant DNA expression vector through the use of appropriate restriction endonucleases. A synthetic IGF-1 analog coding sequence is designed to possess restriction endonuclease cleavage sites at either end of the transcript to facilitate isolation from and integration into these amplification and expression plasmids. The coding sequence may be readily modified by the use of synthetic linkers to facilitate the incorporation of this sequence into the desired vectors by techniques well known in the art. The particular endonucleases employed will be dictated by the restriction endonuclease cleavage pattern of the expression vector to be employed. Restriction sites are chosen so as to properly orient the IGF-1 peptide coding sequence with control sequences to achieve proper in-frame reading and expression of the IGF-1 peptide.

In general, plasmid vectors containing promoters and control sequences which are derived from species compatible with the host cell are used with these hosts. The vector ordinarily carries a replication site as well as marker sequences which are capable of providing phenotypic selection in transformed cells. The IGF-1 peptide coding sequence is positioned so as to be in proper reading frame with the promoter and ribosome binding site of the expression vector, both of which are functional in the host cell in which the IGF-1 peptide is to be expressed. In the preferred practice of the invention, the promoter-operator region is placed in the same sequential orientation with respect to the ATG start codon of DNA sequence encoding the IGF-1 peptide as the promoter-operator occupies with respect to the ATG-start codon of the gene from which it was derived.

Several examples of the expression of IGF-1 peptides as fusion proteins are known in the art. For example, U.S. Pat. No. 5,028,531 (issued Jul. 2, 1991, herein incorporated by reference) describes the preparation of human IGF-1 as a fusion protein. Japanese Patent Application No. 63263085-A (published Oct. 31, 1988) describes the production of human IGF-1 as a fusion protein with the peptide and the subsequent removal of the protecting peptide from the fused IGF-1 to obtain mature IGF-1. Such methodology may be adapted to the production of the IGF-1 peptides of the present invention.

The compounds of Formula 1 may be made either by proceeding through a single-chain BCA or BCAD IGF-1 structure (prepared by solid phase or recombinant means) followed by enzymatic or chemical cleavage. A variety of peptidases (e.g. carboxy-peptidase) are known which cleave a polypeptide at specific sites or digest the peptides from the amino or carboxy termini of the peptide chain. Furthermore, particular chemicals (e.g., cyanogen bromide (CNBr)) will cleave a polypeptide chain at specific sites. Recombinant products devoid of tryptophan residues, such as IGF-1 may be obtained from fusion protein precursors by the incorporation of a codon encoding a tryptophan residue in the precursor fusion protein immediately prior to the first residue of the IGF-1 peptide. For example, DiMarchi, et al. U.S. Pat. No. 4,745,178 issued May 17, 1988, herein incorporated by reference) describes a process for selectively cleaving a peptide or protein at tryptophan residues by treating the peptide in a solution of TFA with an organic sulphoxide at a concentration of 0.14M, HCl at a concentration of 0.12M and water at a concentration of maximally 0.15M–0.55M. The skilled artisan will appreciate the modifications necessary to the amino acid sequence (and synthetic or semi-synthetic coding sequence if recombinant means are employed) to incorporate site-specific internal cleavage sites.

The natural sequence IGF-1 molecule may be obtained free of the characteristic amino-terminal methionine residue by modification of the sequence to incorporate a digestible amino-terminal leader sequence. For example, Hsiung (European Patent Application No. EP-361956-A published Apr. 4, 1990) describes modifications to the DNA sequences encoding protein derivatives to allow expression of small molecular weight proteins and yielding the native protein by cleaving the extra amino acids. Using this method, these extra sequences can be cleaved, e.g. with CNBr or hydroxylamine, to yield the natural protein. For example, DiMarchi, et al. (European patent Application No. EP-220958-A published May 6, 1987) describes the design of peptides of formula: H-X-Pro-IGF1 wherein X is a naturally occurring amino acid. The resultant H-X-Pro-[IGF-1] may be readily cleaved to isolate the native IGF-1 compound or analog by subjecting H-X-Pro-IGF1 to (a) weakly acid conditions in an aprotic solvent or (b) acid, neutral or alkaline conditions in a buffered aqueous medium, to form a diketopiperazine of the H-X-Pro moiety with accompanying cleavage and release of peptide. Similarly, Miller, et al. (European Patent Application No. EP-441955-A published Aug. 21, 1991) disclose the addition of a positively charged leader sequence to the IGF-1 peptide wherein this leader sequences consists of an odd number of lysine, arginine or histidine residues, preferably between 1 and 3 lysine residues which may be subsequently removed using (preferably a diaminopeptidase). Skriver, al. (World Patent application No. WO9203477-A published Mar. 5, 1992) describe the recombinant production of AlaGlu-IGF-1 (AlaGlu amino-terminal extended IGF-1) which may be digested using a diaminopeptidase to produce mature IGF-1.

An example of a method of producing IGF-1 is described in Cain, et al. (U.S. Pat. 5,104,796 published Apr. 14, 1992) which discloses a high titer fermentation process for producing IGF-1.

IGF-1 or analogs may also be recombinantly produced in gram negative bacteria. Wong and Bittner (U.S. Pat. No. 5,084,384) describe a method for producing IGF-1 that entails expression of a gene in gram-negative bacteria, the gene comprising a first DNA sequence encoding a lam B or omp F signal peptide coding sequence operatively linked to a second DNA sequence encoding IGF-1 resulting in the secretion of IGF-1 into the periplasmic space of the bacteria.

The IGF-1 peptides may also be recombinantly produced in eukaryotic expression systems. Grinnell (European Patent Application No. EP-478333-A published Apr. 1, 1992) describes a method for producing IGF-1 under control of the vesicular stomatitis virus promoter (VSV) in eucaryotic cells.

An advantage of eucaryotic expression systems is that it is possible to obtain a secreted protein product. If such a result is desired, it is necessary to modify the coding sequence of the IGF-1 to incorporate a translated signal peptide encoding sequence. Generally, signal peptides are proteolytically cleaved from a residual protein as part of the secretory process in which the protein is transported into the host cell periplasm or culture medium.

It is well known in the art that signal peptides facilitate the extracellular discharge of secretory proteins in both prokaryotic and eukaryotic environments. It has been shown that the addition of a heterologous signal peptide to a normally cytosolic protein will result in he extracellular transport of the normally cytosolic protein in *E. coli.* MacIntyre, et al.,(1987) J. Biol. Chem. 262:8416–8422. It is well known in the art that alternate signal peptide sequences may function with heterologous coding sequences. The recombinant production of such fusion proteins may be accomplished by the addition of a DNA sequence encoding a signal peptide appropriate to the host organism inserted 5to, and in reading frame with, the protein coding sequence.

Signal peptides are well known in the art which could be similarly incorporated into the IGF-1analog structure. In the preferred practice of the invention the signal peptide used is a signal peptide native to a secretory protein of the host cell line. Furthermore, the signal sequence may be wholly synthetic. Host cells may be transformed with the expression vectors of this invention and cultured in conventional nutrient media modified as is appropriate for inducing promoters, selecting transformants or amplifying genes. The culture conditions, such as temperature, pH and the like, are those previously used with the host cell selected for expression, and will be apparent to the ordinarily skilled artisan. The techniques of transforming cells with the aforementioned vectors are well known in the art and may be found in such general references as Maniatis, et al. (1989) *Molecular Cloning: A Laboratory Manual*, Cold Spring Harbor Press, Cold Spring Harbor Laboratory, Cold Spring Harbor, New York or *Current Protocols in Molecular Biology*, Ausubel, et al. eds.(John Wiley and Sons, New York) (1989) and supplements.

In addition to prokaryotes, eukaryotic microbes such as yeast cultures may also be used. Saccharomyces cerevisiae, or common baker's yeast is the most commonly used eukaryotic microorganism, although a number of other strains are commonly available. For expression in Saccharomyces, the plasmid YRp7, for example, (ATCC-40053, Stinchcomb, et al., (1979) Nature 282:39; Kingsman et al. [1979] Gene 7:141; Tschemper et al., [1980] Gene 10:157) is commonly used. Barr, et al. (Chiron Corporation, U.S. Pat. No. 427233? issued Nov. 1, 1984) describes a method for the recombinant production of human IGF-1 in yeast. This method comprises growing host cells containing a structural gene encoding IGF-1 joined in proper reading frame with secretory leader and processing signal sequences recognized by the host and isolating secreted human IGF from the media. Similarly, Bayne and Cascieri (European Patent Application No. EP-379338-A published Jul. 25, 1990) describes a method for the recombinant production of human IGF analogs in yeast. Hollenberg and Strasser (European Patent Application No. EP-394538-A published Oct. 31, 1990) describe a transformed Schwanniomyces yeast cells capable of producing IGF-1 or analogs thereof.

Formulations of IGF-1 peptide compounds may be designed in reference to general principles in the formulation such as those found in *Peptide and Protein Drug Delivery*, Lee, V. H. ed. (1991) Marcel-Dekker, N.Y.

For example, IGF-1 analogs of Formula 1 can be admixed with conventional pharmaceutical carriers and excipients and used in the form of tablets, capsules, elixirs, suspensions, syrups, wafers and the like. The compositions comprising IGF-1 analog compounds will contain from about 0.1 to 90% by weight of the active compound, and more generally from about 10 to 30%. The compositions may contain common carriers and excipients such as corn starch or gelatin, lactose, sucrose, microcrystalline cellulose, kaolin, mannitol, dicalcium phosphate, sodium chloride, and alginic acid. Disintegrators commonly used in the formulations of this invention include croscarmellose, microcrystalline cellulose, corn starch, sodium starch, glycolate and alginic acid. Tablet binders that can be included are acacia, methyl cellulose, sodium carboxymethylcellulose, polyvinylpyrrolidone (Povidone), hydroxypropyl methylcellulose, sucrose, starch and ethylcellulose. Lubricants that can be used include magnesium stearate or other metallic stearates, stearic acid, silicone fluid, talc, waxes, oils and colloidal silica. Flavoring agents such as peppermint, oil of wintergreen, cherry flavoring, or the like can also be used. It may be desirable to add a coloring agent to make the dosage form more attractive in appearance or to help identify the product.

For intravenous (IV) use, a water soluble form of compounds of Formula 1 can be dissolved in one of the commonly used intravenous fluids and administered by infusion. Such fluids, for example, physiological saline, Ringer's solution or 5% dextrose solution can be used. Finkenaur (U.S. Pat. No. 4,179,497) describes an aqueous medicinal composition containing IGF-1 and a water-soluble polysaccharide to stabilize the peptide against loss of biological activity.

For intramuscular preparations, a sterile formulation of a suitable soluble salt form of the compounds of Formula 1, for example the hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

For oral use, a sterile formulation of a suitable salt form of IGF-1 analog, for example, the hydrochloride salt, formulated in a diluent such as distilled or deionized water, is particularly useful.

In some instances, it may be desirable to administer the compounds of Formula 1 intranasally. Formulations useful in the intranasal absorption of IGF-1 are well known in the art. For example, Japanese Patent Application No. J02078632-A (published Mar. 19, 1990) describes a nasal formulation for IGF-1. Such formulations comprise 0.1–10% IGF-1 and 0.05 –2 wt. % carboxyvinyl polymer. Japanese Patent Application No. J02000214-A (published Jan. 5, 1990) also describes a nasal preparation for treatment of dwarfism containing insulin-like growth factor I and sucrose fatty acid ester.

In some therapeutic applications, it may be desirable to achieve a prolonged release of the compound. Methods of incorporating the compounds of Formula 1 into such delayed release formulations are well known in the art and may be found in general texts on the subject. For example, Geistlich (World Patent Application No. WO9003810-A published Apr. 19, 1990) describes a delayed release composition for wound healing comprising a hydrogel swollen with an aqueous solution containing IGF-1 and/or other growth factors. These compositions are generally used in sheet form for wound dressings, in surgery in preparation of the wound base for free skin transplantation, in the treatment of the donor site after removal of split skin grafts in plastic surgery, and for covering superficial operation wounds to prevent exposed bradytrophic tissue from drying out. Furthermore, Chu, et al. (U.S. Pat. No. 4,950,483 issued Aug. 21, 1990) describes a collagen implant comprising IGF-1 and/or other growth factors useful for promoting wound healing and releasing bioactive agents.

Alternatively, the unit dosage form of the compound can be a solution of the compound, preferably in its salt form, in a suitable diluent in sterile hermetically sealed ampoules. The concentration of the compound in the unit dosage may vary, e.g. from about 1% to about 50% depending on the particular form of the compound and its solubility and the dose desired by the physician.

In practicing this method, compounds of Formula 1 can be administered in a single daily dose or in multiple doses per day. The treatment regime may require administration over extended periods of time. The amount per administered dose or the total amount administered will depend on such factors as the nature and severity of the disease, the age and general health of the patient and the tolerance of the patient to the compound. The method comprises administering to the organism an effective amount of IGF-1 analog in a dose between about 1 and 1000 µg/kg. A preferred dose is from about 10 to 100 µg/kg of active compound. A typical daily dose for an adult human is from about 0.5 to 5 mg. A convenient method of practicing the treatment method is to administer the compounds of the Formula 1 via intravenous infusion. In this procedure a sterile formulation of a suitable soluble salt of the compound is incorporated in a physiological fluid, such as 5% dextrose solution, and the resulting solution is infused slowly IV. Alternatively, the piggyback method of IV infusion can also be used. Much like insulin therapy IGF-1 and analogs thereof can be more conveniently administered by subcutaneous intramuscular injection.

Another preferred formulation of the compounds of the present invention is the use of transdermal patches. Such transdermal patches may be used to provide continuous or discontinuous infusion of the compounds of the present invention in controlled amounts. The construction and use of transdermal patches for the delivery of pharmaceutical agents is well known in the art. Such patches may be constructed for continuous, pulsatile, or on demand delivery of pharmaceutical agents.

The pharmaceutical formulations comprising the compounds of Formula 1 described above may be administered to an organism for therapeutic effects. IGF-1 has known insulin-like potency and stimulation potency of sulphate uptake by cartilage, and it may enhance protein and DNA synthesis in cells. The compounds of the present invention are therefore useful as a growth promoter and for the treatment of diabetes. They may be used in humans to treat growth hormone deficiencies, in farm animals to increase growth rates, increase the relative proportion of muscle or improve food conversion efficiency, in humans to suppress the loss of body protein in severe catabolic states such as following burns, infection or other trauma, in humans and animals to improve wound healing and to support the growth of cells in culture. They may be used for the treatment of disorders associated with tissue wasting including burns, skeletal trauma, infection, cancer, cystic fibrosis, Duchenne muscular dystrophy, osteoperosis, Becker dystrophy, autosomal recessive dystrophy, polymyositis as well as other myopathies and AIDS. The compounds of the present invention may also be used in the treatment of protein accumulation deficiencies in mammals. Specific deficiencies are those associated with infant prematurity, growth hormone deficiency, somatomedin deficiency, burns, infection, other trauma, cancer, cystic fibrosis, Duchenne muscular dystrophy, Becker dystrophy, autosomal recessive dystrophy, polymyositis and other myopathies. They are also useful as agents to stimulate erythropoiesis and are therefore useful in humans for treating growth deficiencies and for restricting negative nitrogen balance associated with catabolic conditions. Froesch, et al. (U.S. Pat. No. 5,106,832) describes the use of pharmaceutical formulations comprising IGF-1 for use in improving glomerular filtration and renal plasma flow and can be used for the treatment of patients suffering from renal diseases and for the preparation of therapeutic combinations for treatment of renal diseases. The IGF-1 analogs of the present invention would be similarly useful. World Patent Application No. WO9118621–1 published Dec. 12, 1991) describes a method for enhancing growth of a mammal using a combination of growth hormone and IGF-1 and/or analogs thereof, allowing lower doses of GH to be used when compared to the enhancement in growth achieved using an equivalent dose of IGF-1 or GH alone. The IGF-1 analogs of the present invention would be similarly useful. Such combination therapy is also useful in the treatment of diabetes where hyperinsulinemia/hyperglycaemia produces a reduced anabolic effect when treated with GH alone.

EXAMPLES

Example 1.

Preparation of IGF-1 A Domain ("A") $(S-SO_3^-)_4$

The solid phase synthesis of the peptide (0.5 mMole scale) was carried out using 0.63 g of Boc-Ala-PAM resin on an Applied Biosystems 430A peptide synthesizer (commercially available from Applied Biosystems, Foster City, Calif.) using double coupling and acetic anhydride capping cycles. Arginine was coupled using preformed hydroxy benzotriazole esters. All other amino acids were couple using preformed symmetrical anhydrides with DCC.

The peptidyl resin [containing Met(O)] was reduced (to Met) using the procedure of DiMarchi, et al, U.S. Pat. No. 4,853,254 (the entire teaching of which is hereby incorporated by reference), where the peptidyl resin was suspended at about 1 mg/ml in TFA followed by the addition of dimethyl sulfide (10% by volume) and 12M HCl (1% by volume). After reacting for 1 hour, the sample was filtered, washed with $CH_2Cl_2$ and vacuum dried at room temperature.

The peptide was deprotected and cleaved from the resin with 20 ml of anhydrous HF containing 5% meta-cresol and 5% para-thiocresol at 0° C. for one hour. After removal of volatiles by vacuum distillation, the peptide/resin was washed with ethyl ether and vacuum dried.

The peptide/resin was sulfitolyzed by addition of 50 ml of 8M guanidine HCl containing 0.2M tris, 0.1M sodium tetrathionate, and 0.1M sodium sulfite and stirred vigorously at pH 8.6 for three hours.

After removal of the cleaved resin by filtration, the sample was desalted using a 3×87 cm Pharmacia G-10 Sephadex® column and 0.05M ammonium bicarbonate. The desired fractions were pooled and lyophilized.

The peptide was dissolved in 40 ml of 0.1M ammonium bicarbonate and purified over a 2.12×25 cm DuPont Zorbax® C8 reverse phase HPLC column using a linear gradient of acetonitrile in 0.1M ammonium bicarbonate. Appropriate fractions were pooled and lyophilized.

Example 2.

Preparation of IGF-1 $BC^{10}$ Domain $(S-SO_3^-)_2$

The solid phase synthesis of the peptide (0.5 mMole scale) was carried out using 0.66 g of Boc-Pro-PAM resin on an Applied Biosystems 430A peptide synthesizer using double coupling and acetic anhydride capping cycles. Arginine, asparagine and glutamine were coupled using preformed hydroxy benzotriazole esters. All other amino acids were coupled using preformed symmetrical anhydrides with DCC.

The peptide was deprotected and cleaved from the resin with 25 ml of anhydrous HF containing 10% meta-cresol at 0° C. for one hour. After removal of volatiles by vacuum distillation, the peptide/resin was washed with ethyl ether and vacuum dried.

The peptide/resin was sulfitolyzed by addition of 50 ml of 8M guanidine HCl containing 0.2M tris, 0.1M sodium tetrathionate, and 0.1M sodium sulfite and stirred vigorously at pH 8.6 for three hours.

After removal of the cleaved resin by filtration, the sample was desalted using a 3×87 cm Pharmacia G-10 Sephadex® column and 0.05M ammonium bicarbonate. The desired fractions were pooled and lyophilized.

The peptide was dissolved in 40 ml of 0.1M ammonium bicarbonate and purified over a 2.12×25 cm DuPont Zorbax® C8 reverse phase HPLC column using a linear gradient of acetonitrile in 0.1M ammonium bicarbonate. Appropriate fractions were pooled and lyophilized.

Example 3.

Disulfide Pairing of $BC^{10}$,A (Chain Combination)

21 mg of lyophilized $BC^{10}$ S-sulfonate (prepared in accordance with in Example 2) was combined with 18 mg IGF-1 A domain $(S-SO_3^-)$. (prepared as in Example 1 above) in substantial accordance with the procedure of Chance, et al., "The Production of Human Insulin Using Recombinant DNA Technology and a New Chain Combination Procedure", in *PEPTIDES: Synthesis-Structure-Function*, Rich, D. H., and Gross, E., eds. (1981) Pierce Chemical Co. Rockford, Ill. pgs 721–728. The respective peptides were each dissolved at about 7 mg/ml in 0.1M glycine, pH 10.5, filtered, chilled to 4° C. and combined following addition of 155 µl of 0.1M DTT in 0.1M glycine. After stirring at 4° C. for 24 hours, the reaction was quenched by adjusting the pH to 3 with HCl.

Example 4.

Purification of $BC^{10}$,A

The quenched (acidified) chain combination sample was partially purified and desalted by loading onto and eluting from a 2.6×56 cm Pharmacia Sephadex® G-50SF column. Elution was performed at 4° C. using 1M HOAc. Selected fractions were pooled and further purified over a 0.46×25 cm DuPont Zorbax® C8 column at room temperature using a linear gradient of acetonitrile in 0.1M $NaH_2PO_4$, pH 2.3. The desired fractions were diluted two-fold with purified water and desalted using a Waters C18 SepPak® (Milford, Mass.). The sample was eluted using 0.1% TFA in 50% acetonitrile. The eluent was lyophilized to yield 0.5 mg of pure protein. The identity of the material was confirmed by amino acid analysis and Fast Atom Bombardment Mass Spectrometry (FAB/MS)

Results of the FAB/MS gave a molecular weight of 6643 (Theoretical 6644). Amino acid composition was as follows based on aspartic acid as molar unity: Asp 5.0(5); Thr 2.0(2); Ser 4.0(4); Glu 5.2(5); Pro 3.3(3); Gly 7.4(7); Ala 4.2(4); ½ Cys 4.9(6); Val 2.7(3); Met 0.73(1); Ile 0.65(1); Leu 5.1(5); Tyr 2.9(3); Phe 4.0(4); Lys 1.1(1); Arg 5.9(6);

Example 5.

IGF-1 and Insulin Radioreceptor Assay Procedure

Measurement of insulin and IGF-1 activity was accomplished in substantial accordance with the teaching of Gruppuso, et al. (1988) J. of Clin. Endocrin. and Metab. 67:194–197. Briefly, 30–50 µg of human placental membrane protein was incubated with approximately 10 femtomoles of [$^{125}$I] ligand in a final volume of 500 µl of 100 mM HEPES, pH 7.8, 120 mM NaCl, 5 mM KCl, 1.2 mM MgSO$_4$, 8 mM glucose and 0.25% BSA for 24 hours at 4° C. Membranes were collected on glass fiber filters pretreated with 0.1% polyethyleneimine by using a cell harvester (Skatron, Lier, Norway). Binding data were analyzed by fitting displacement curves to a four parameter model employing Prefit/Allfit® software for the determination of EC$_{50}$ values.

---

---

We claim:

1. An IGF-1 analog of the formula:

$$BC^n A \quad (1)$$

wherein:

B is the B domain of IGF-1 or a functional analog thereof,

C is the C domain of IGF-1 or a functional analog thereof, n is the number of amino acids in the C domain and is from about 6 to about 12, and A is the A domain of IGF-1 or a functional analog thereof.

2. The compound of claim 1 wherein B, C, and A are derived from human IGF-1.

3. The compound of claim 2 wherein in n=8.

4. The compound of claim 2 wherein n=10.

5. The compound of claim 2 wherein n=12.

6. A pharmaceutical formulation comprising a therapeutically effective quantity of the compound of claim 1.

7. The pharmaceutical formulation of claim 6 wherein said compound is the compound of claim 4.

8. A method of treating an individual afflicted with a condition selected from the group consisting of diabetes, diabetic neuropathy, insulin-resistance, IGF-Resistance, GH-Deficiency, renal failure, cancer, AIDS, sepsis, or osterporosis comprising the administration of a pharmaceutically effective amount of the compound of claim 1.

9. The method of claim 8 wherein B, C, and A are derived from human IGF-1 and n=10.

\* \* \* \* \*